United States Patent [19]

Vertesy et al.

[11] Patent Number: 5,459,141
[45] Date of Patent: Oct. 17, 1995

[54] COMPOUNDS 31668P AND 31668U, A PROCESS FOR THEIR PRODUCTION AND THEIR USE

[75] Inventors: Lásló Vertesy, Eppstein/Ts; Joachim Betz, Frankfurt am Main; Hans-Wolfram Fehlhaber, Idstein; Matthias Helsberg; Herbert Kogler, both of Kelkheim/Ts; Michael Limbert, Hofheim/Ts; Dieter-Andreas Sukatsch, Frankfurt am Main, all of Germany; Ramaiyer R. Chandran, Thane; Bimal N. Ganguli, Bombay, both of Ind.

[73] Assignee: Hoechst Aktiengesellschaft, Frankfurt, Germany

[21] Appl. No.: 77,985

[22] Filed: Jun. 17, 1993

[30] Foreign Application Priority Data

Jun. 19, 1992 [EP] European Pat. Off. ............ 92110366

[51] Int. Cl.$^6$ ................. C07D 471/22; A61K 31/495
[52] U.S. Cl. ................ 514/250; 435/119; 435/253.5; 544/338
[58] Field of Search ............... 514/250; 544/338

[56] References Cited

U.S. PATENT DOCUMENTS 4,003,902  1/1977  Kluepfel et al. ................ 544/338

OTHER PUBLICATIONS

CRC Handbook of Antibiotic Florida, 1980, vol. III, pp. 35–78.
CRC Handbook of Antibiotic Florida, 1980, vol. XIII, part 2, pp. 163–229.

Patent Abstracts of Japan, vol. 13, No. 384 (C–629) citing JP A–1–132585 (1989).

*Primary Examiner*—Mark L. Berch
*Attorney, Agent, or Firm*—Barbara V. Maurer

[57] ABSTRACT

Compounds 31668P and 31668U, a process for their production and their use.

Compound 31668P and compound 31668U with the formulae

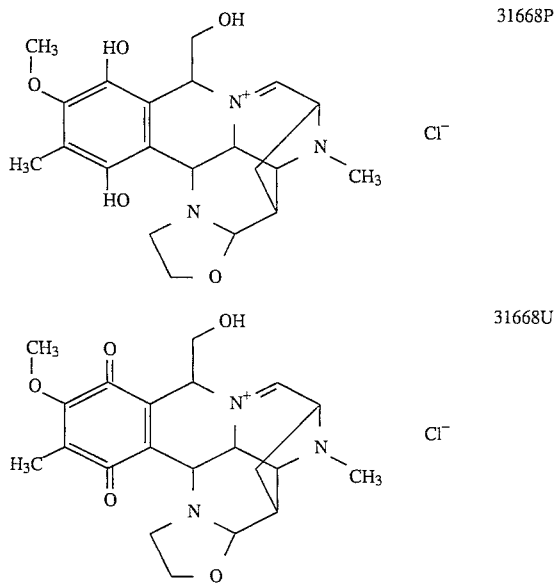

have an antibiotic and an antitumor action.

5 Claims, No Drawings

COMPOUNDS 31668P AND 31668U, A PROCESS FOR THEIR PRODUCTION AND THEIR USE

Compounds 31668P and 31668U, a process for their production and their use.

This invention relates to antibacterial antibiotics 31668P and 31668U, their pharmaceutically acceptable salts, a process for their production and their use.

Antibiotics 31668P and 31668U may be described as antibacterial antibiotics belonging to the quinonoid class. The said antibiotics are active against a large number of both gram-positive and gram-negative bacteria. Quinonoid class of antibiotics are described in CRC Handbook of Antibiotic compounds by J. Berdy, Vol. III (CRC Press INC. Florida 1980) and Vol. XIII, part 2, pages 35–78 and 161–230 (CRC press INC. Florida, 1987). Furthermore, said antibiotics have cytotoxic activity.

Compounds 31668P and 31668U described herein differ from all the known antibiotics in their molecular formulae and therefore form the subject of this invention. Furthermore, a chemical abstract on-line search performed with the search keys of molecular weight and molecular formula confirms the novelty of 31668P and 31668U.

Compounds 31668P und 31668U have the following formulae

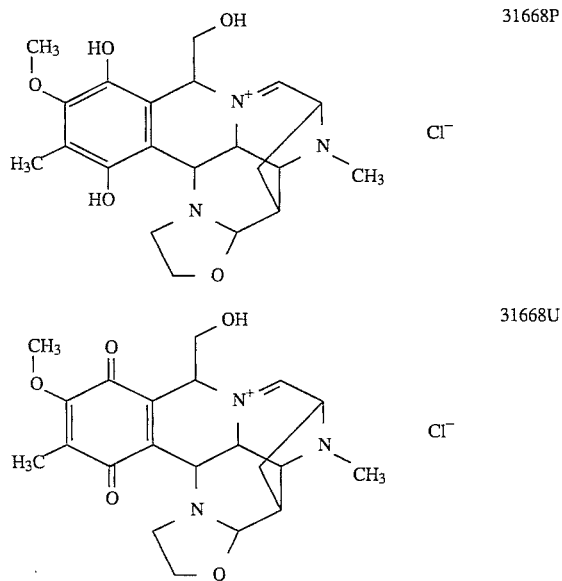

The microorganism, culture number Hoechst India Limited Y-90,31668 henceforth referred to as Y-90,31668 used for the production of 31668P and 31668U, was isolated from a soil sample collected at Bharatpur Bird Sanctuary, Rajasthan, India. The microorganism Y-90,31668 belongs to the genus Streptomyces. Said microorganism has been deposited with Deutsche Sammlung von Mikroorganismen, Braunschweig under the conditions of the Treaty of Budapest on May 6, 1992 (DSM 7065).

Another object of the present invention is to provide a process for the production of new antibiotics 31668P and 31668U from a microbial strain viz. streptomycete species Y-90,31668 (culture number Hoechst India Limited Y-90, 31668), its mutants or variants.

Said process consists of cultivating the said microbial strain, its mutants or variants in a nutrient medium by fermentation, preferably under aerobic conditions at 26°–32° C. and pH 6 to 8 and isolating and purifying 31668P and 31668U from the culture broth in a known manner and if desired, converting the 31668P and 31668U into their pharmaceutically useful salts in a known manner.

The nutrient medium includes carbon sources such as starch, glucose, sucrose, dextrin, fructose, molasses, glycerol, lactose or galactose. The preferred carbon source is glucose. The nutrient medium also includes nitrogen sources such as soybean meal, peanut meal, yeast extract, beef extract, peptone, malt extract, corn steep liquor, gelatin or casamino acids. The preferred nitrogen source is soybean meal. The nutrient medium also includes nutrient inorganic salts such as calcium carbonate, and trace elements such as cobalt chloride.

Particularly preferred is the fermentation at 28° C. (±1° C.) and pH about 7.2.

The fermentation is preferably carried out for 40 to 60 hours when optimal yield of the antibiotic of the present invention is found to have been obtained.

The fermentation is, particularly preferred, carried out for about 48 hours under submerged conditions in shake flasks as well as in laboratory fermenters.

The progress of the fermentation and formation of the antibiotic of the present invention can be detected by High Pressure Liquid Chromatography (HPLC) and by measuring the bioactivity of the culture broth against *Staphylococcus* and *Escherichia* species by the known microbial agar plate diffusion assay method. The preferred cultures are *Staphylococcus aureus* 209P and *Escherichia coli* 9632.

31668P and 31668U can be isolated from the culture broth by direct adsorption on suitable adsorbents like activated carbon, Diaion HP-20® (high porosity resin based on a polystyrene-divinylbenzene copolymer-Mitshubishi Chemical Industries, Japan) or Amberlite XAD® (porous resin based on polystyrene-acrylic acid ester -Rohm & Haas Co., U.S.A.). The preferred adsorbent is Diaion HP-20®. 31668P and 31668U can be eluted out of these adsorbents using mobile phases such as water, methanol, acetone or acetonitrile or combinations thereof containing suitable additive such as salt or acid. The preferred eluant is aqueous methanol containing acid.

The aforementioned active eluates containing 31668P and 31668U are concentrated and can be further purified in a number of ways. For example, readsorption and elution process with activated charcoal, Amberlite XAD-4 and 7®, Diaion HP-20®; gel filtration with Sephadex LH-20®, or Sephadex G® series gels (Pharmacia Fine Chemicals AB, Sweden) using water, methanol, acetone or combinations thereof as eluants; ion-exchange chromatography with IRC-50 ($H^+$), S-Sepharose® Fast Flow (Pharmacia) or Fractogel EMD® SO-. The preferred method of purification includes MPLC on S-Sepharose FF using phosphate buffer with suitable pH as the eluant.

Another subject of the instant invention are the chemical equivalents of the compounds 31668P and 31668U; said equivalents are in particular the salts with the anions of other organic or inorganic acids such as $H_2SO_4$, citric acid, lactic acid, succinic acid or acetic acid, which can be produced in a known manner.

The physico-chemical and spectral properties of 31668P and 31668U are given below:

|  | 31668P | 31668U |
|---|---|---|
| Colour: | Deep Yellow | Orange |
| Nature: | Basic | Basic |

-continued

|  | 31668P | 31668U |
|---|---|---|
| Molecular formula: | $[C_{21}H_{28}N_3O_5]^+$ Cl<br>(HR FAB-MS) | $[C_{21}H_{26}N_3O_5]^+$ Cl<br>(HR FAB-MS) |
| UV max: | 292 nm<br>($PO_4$ buffer, pH 5) | 268 nm<br>(MeOH) |

Biological properties of 31668P and 31668U

The antibacterial activity of 31668P and 31668U as Minimum Inhibitory Concentration values required to inhibit the growth of various bacteria are shown in Table 1.

The said antibiotics inhibit the growth of Hela cells in cell culture in concentration < 1 microgram/ml. The vero cell culture shows a remarkable cytostatic effect in a concentration range of 0.01–3.6 microgram/ml.

TABLE 1

Minimal inhibitory concentrations of the anitbiotics 31668P and 31668U determined by the broth-dilution tests against selected strains of bacteria (microgram per ml)

| Staph. aureus SG 511 | <0.002 | <0.002 |
|---|---|---|
| Staph. aureus 285 | <0.002 | <0.002 |
| Staph. aureus 503 | <0.002 | <0.002 |
| Strept. pyogenes 308 A | <0.002 | <0.002 |
| Strept. pyogenes 77 A | <0.002 | <0.002 |
| Strept. faecium D | 0.025 | 0.195 |
| Pseud. aeruginosa ATCC 9027 | 0.781 | 6.250 |
| Pseud. aeruginosa 1592 E | 0.781 | 6.250 |
| Pseud. aeruginosa 1771 | 1.560 | 12.500 |
| Pseud. aeruginosa 1771 M | 0.391 | 1.560 |
| E. coli 078 | 0.049 | 0.195 |
| E. coli TEM | 0.195 | 1.560 |
| E. coli 1507 E | 0.195 | 3.130 |
| E. coli DC 0 | 0.781 | 6.250 |
| E. coli DC 2 | 0.195 | 0.781 |
| Salm. typhimurium | 0.391 | 3.130 |
| Klebs. spec. 1082E (K-1) | 0.391 | 0.781 |
| Klebs. spec. 1522 E | 0.391 | 1.560 |
| Enterobact. cloacae P 99 | 0.195 | 1.560 |
| Enterobact. cloacae 1321 E | 0.098 | 0.195 |

As shown above compounds 31668P and 31668U have an antibiotic activity, they also show—as already mentioned—a cytostatic effect.

Accordingly, another object of the instant inventions are pharmaceuticals containing the said compounds. The pharmaceuticals containing an active amount of the said compounds can be prepared and administered in a manner known per se. The preferred use of these pharmaceuticals is the combat of bacterial infections and of malignant tumors.

In the following examples and in the patent claims the instant invention will be further characterized.

Example 1

Isolation of the culture Y-90,31668 from soil
(a) Composition of nutrient isolation medium

| Corn starch | 10.0g |
|---|---|
| Casein | 1.0g |
| Peptone | 1.0g |
| Yeast Extract | 1.0g |
| $K_2HPO_4$ | 0.5g |
| Agar powder | 13.0g |
| Demineralized water | 1000 ml |
| pH 7.5 | |

(b) Soil plating and isolation 10 g of soil collected from Bharatpur Bird Sanctuary, Rajasthan, India was added to 90 ml of sterilized demineralized water in a 250 ml Erlenmeyer flask which was shaken for 2 hours on a rotary shaker (220 rpm). The above soil suspension was then serially diluted in steps of 10 up to $10^{-5}$. From the last dilution, 1 ml of suspension was placed at the center of a sterile glass petri plate (15 cms diameter) to which was then approximately 50 ml of the above isolation medium supplemented with 25 mcg/ml of amphotericin B as antifungal agent and cooled to 45° C. and the plate swirled thoroughly. The mixture of soil suspension and medium was allowed to settle and incubated at 28° C. (±1° C.) for 7 days. The petri plate was periodically observed and the culture No. Y-90,31668 was isolated from amongst the growing microorganisms.

Example 2

Maintenance of the culture Y-90,31668
Composition of maintenance medium
Culture No. Y-90,31668 was maintained on the following medium:

| Malt Extract | 10.0g |
|---|---|
| Yeast Extract | 4.0g |
| Glucose | 4.0g |
| Agar Powder | 15.0g |
| Demineralized water | 1000 ml |
| pH 7.0 | |

After dissolving the ingredients thoroughly by heating, it was distributed in test tubes and then sterilized at 121° C. for 20 minutes. The test tubes were cooled and allowed to solidify in a slanting position. The agar slants were streaked with the growth of the culture No. Y-90,31668 by a wire loop and incubated at 28° C. (±1° C.) until a good growth was observed. The well grown cultures were stored in the refrigerator at +8° C.

Example 3

Fermentation of culture Y-90,31668
Composition of seed medium

| Glucose | 15.0g |
|---|---|
| Soybean meal | 15.0g |
| Corn steep liquor | 5.0g |
| $CaCO_3$ | 2.0g |
| NaCl | 5.0g |
| Demineralized water | 1000 ml |
| pH 7.2 | |

The above seed medium was distributed in 80 ml amounts in 500 ml Erlenmeyer flasks and autoclaved for 20 minutes. The flasks were cooled to room temperature and each flask was then inoculated with a loopful of the above mentioned well grown culture of example 2 and shaken on a rotary shaker for 72 hours at 220 rpm at 28° C. (± 1° C.) to give seed culture.

Composition of the production medium

| Glucose | 20.0g |
|---|---|
| Soybean meal | 10.0g |
| $CaCO_3$ | 0.2g |

-continued

| | |
|---|---|
| CoCl$_2$.6H$_2$O | 0.001g |
| Demineralized water | 1000 ml |
| pH 7.2 | |

200 liters of the production medium in 300 liter fermenter was sterilized and seeded with 4% (v/v) of the seed culture mentioned above.

The fermentation was run with the following parameters:

| | |
|---|---|
| Temperature | 28° C. (±0.5° C.) |
| Agitation | 300 rpm |
| Aeration | 0.5–1.0 vvm |
| Harvest time | 40–48 hrs. |

The production of the antibiotic was monitored by the bioactivity against Staphylococcus aureus 209P. When fermentation was discontinued, the pH of the culture broth was 7.0. The culture broth was centrifuged after harvesting and the antibiotic 31668P and 31668U were isolated and purified from the culture filtrate as described below.

Isolation and purification of 31668P and 31668U

Approximately 180 L of the harvested broth, as obtained in example 4, was separated from the mycelium by centrifugation. The resulting broth filtrate was passed through a column of 15 L of Diaion HP-20® in water. The column was washed with 30 L of demineralized water. Desorption was then carried out with 0–50% aqueous methanol containing 0.1M acetic acid. Fractions of 5 L each were collected.

On the basis of antibiotic activity two components could be eluted. 31668P was eluted in 5–10% aqueous methanol containing 0.1M acetic acid while 31668U got eluted in 20–40% aqueous methanol containing 0.1M acetic acid.

Isolation and purification of 31668P and 31668U is given below in a flow sheet form.

Isolation and purification of the antibiotics 31668P
180 l culture filtrate, pH 7.0
Adsorption on 15 l HP-20 in a column (15cm×85 cm diameter×length), washing with 30 l deionized water, desorption by a gradient water against 0, 1M acetic acid subsequently against 50% methanol in 0, 1M acetic acid, 
Fractionation, 5 l each,
Eluate with 0, 1M acetic acid, 5–10% methanol, crude polar activity, in 10 l, passing through a column, containing 3 l S-Sepharose FF, equilibrated with 10 mM phosphat buffer, pH 3, elution with 50 mM phosphate buffer, pH 7,5, fractions: 0,5 l
active fractions, pH 6–7, 1,0 l decolorization, by passing through DEAE-Sepharose FF, pH 7,0 yellow active effluent concentration in vacuo, chromatography on Select B RP-18 (E. Merck, 32 mm×250 mm inside diameter× length), loading at pH 5, washing with deionized water, desorption with 0, 1% acetic acid in water, lyophilization of the active fractions 31668P, as acetate salt, 21 mg.
Yellow powder.
Isolation and purification of the antibiotics 31668U 180 l culture filtrate, pH 7.0 adsorption on 15 l HP-20 in a column (15cm×85 cm diameter×length), washing with 30 l deionized water, desorption by a gradient water against 0.1M acetic acid subsequently against 50% methanol in 0, 1M acetic acid, fractionation, 5 l each.

Eluate with 0, 1M acetic acid, 20–40% methanol, crude unpolar activity, in 15 l passing through a column containing, 3 l S-Sepharose FF, equilibrated with 10 mM phosphat buffer, pH 3, elution with 50 mM phosphate buffer, pH 7,5, fractions 0,5 l active fractions, pH 6–7, 1,5 l decolorization, by passing through DEAE-Sepharose FF, pH 7,0 yellow active effluent concentration in vacuo, chromatography on Select B RP-18 (E. Merck, 32 mm×250 mm inside diameter×length), loading at pH 5, washing with deionized water, desorption with a gradient 0, 1% trifluoracetic acid (TFA)/10% acetonitrile in 0,1% TFA, lyophilization of the active fractions 31668U, as TFA salt, 60 mg.

Orange powder.

We claim:

1. Compounds having the formulas

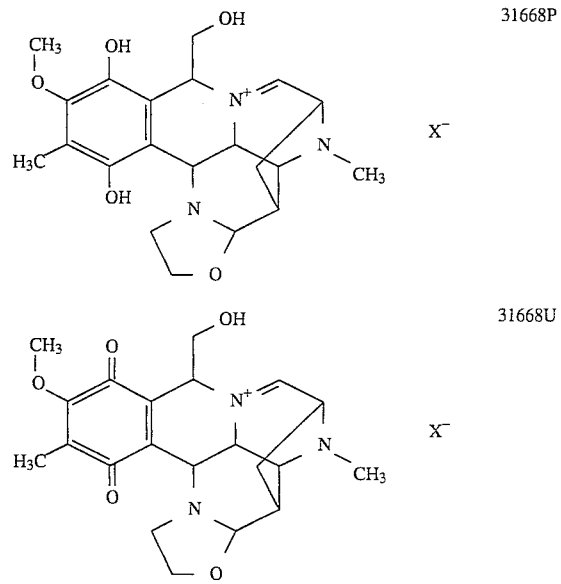

wherein $X^e$ is the anion of a pharmaceutically acceptable organic or inorganic acid.

2. The compound of claim 1 wherein the acid is sulfuric acid, hydrochloric acid, citric acid, lactic acid, succinic acid or acetic acid.

3. The compound of claim 1 wherein $X^-$ is $Cl^-$.

4. A pharmaceutical composition which comprises a pharmaceutically acceptable carrier and an antibiotically effective amount of the compound of claim 1.

5. A method for controlling bacterial microorganisms which comprises administering to a patient in need thereof an antibiotically effective amount of the compound of claim 1.

* * * * *